(12) United States Patent
Shennib et al.

(10) Patent No.: US 6,251,116 B1
(45) Date of Patent: Jun. 26, 2001

(54) DEVICE FOR INTERCONNECTING VESSELS IN A PATIENT

(75) Inventors: Hani Shennib, Quebec (CA); Michael Mack, Dallas, TX (US); Amr Salahieh, Campbell (CA); Jodi Akin, Walnut Creek; Jackson Demond, Santa Cruz, both of CA (US)

(73) Assignee: Vasconnect, Inc., Walnut Creek, CA (US)

( * ) Notice: Subject to any disclaimer, the term of this patent is extended or adjusted under 35 U.S.C. 154(b) by 0 days.

(21) Appl. No.: 09/363,309

(22) Filed: Jul. 28, 1999

(51) Int. Cl.[7] .................................................. A61B 17/04
(52) U.S. Cl. ........................... 606/155; 606/153; 606/154
(58) Field of Search ..................................... 606/139, 153, 606/154, 155; 623/11, 12

(56) References Cited

U.S. PATENT DOCUMENTS

| 5,141,516 | 8/1992 | Detweiler | 606/154 |
| 5,797,934 | 8/1998 | Rygaard | 606/153 |
| 5,868,763 | 2/1999 | Spence et al. | 606/153 |

FOREIGN PATENT DOCUMENTS

| 0894475A1 | 2/1999 | (EP) . |
| WO 98/02099 | 1/1998 | (WO) . |
| WO 98/16174 | 4/1998 | (WO) . |
| WO 98/52474 | 11/1998 | (WO) . |

Primary Examiner—Gary Jackson
(74) Attorney, Agent, or Firm—Bret E. Field; Bozicevic, Field & Francis

(57) ABSTRACT

The present invention provides an implant device and an associated method for interconnecting human vessels rapidly, safely and in a minimally invasive manner. The device comprises a first segment, a second segment, and a flow opening along the periphery of the two connected segments. The first and second segments are bendable for easy insertion into an incision made within each vessel. Upon release, each bendable segment subsequently conforms to the interior walls of a vessel to provide a sealing contact along the contact surface of the segment inserted within. The flow opening provides fluid interconnectivity between the vessels connected by the implant device. The device is configured so as to: (1) not impede flow inside a vessel; (2) prevent flow out of the openings in the vessels except for flow from one vessel to another via the connector opening; and (3) force the vessels toward each other at areas around the openings allowing the vessels to grow together so that flow in one vessel may flow to the other. The implant device may be inserted using special catheter designed specifically for the placement and release of the implant device within the vessels for interconnection thereof. The implant device is preferably provided in an assortment of sizes, shapes, configurations, etc. in order to interconnect vessels of various sizes, shapes and orientations. A system which includes a catheter having the implantable device loaded therein is also disclosed

20 Claims, 6 Drawing Sheets

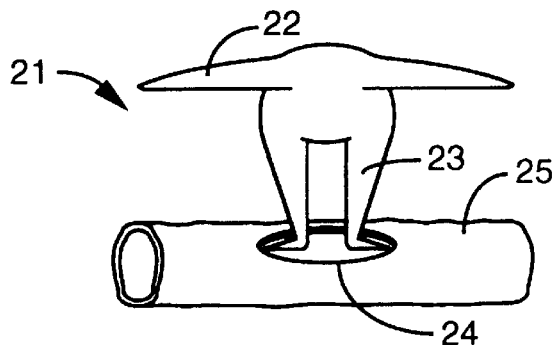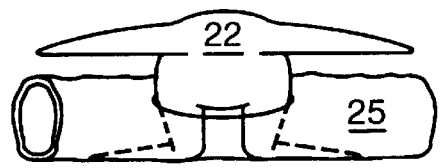
FIG. 4A　　　　　FIG. 4B
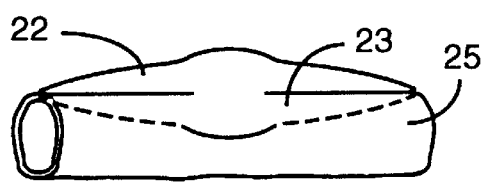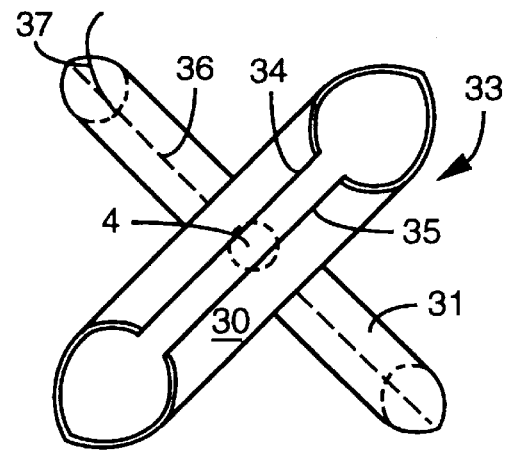
FIG. 4C　　　　　FIG. 5
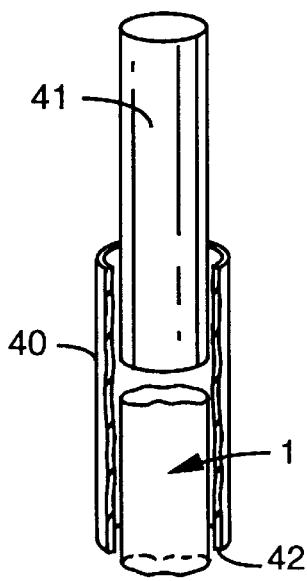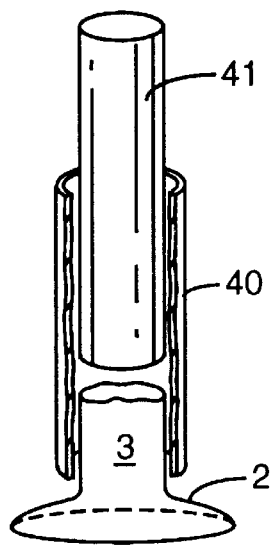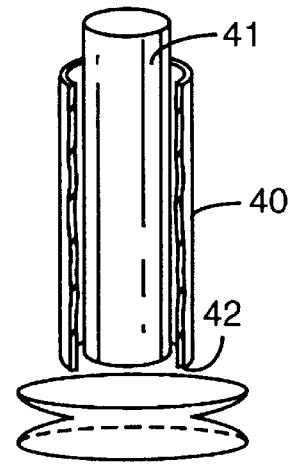
FIG. 6A　　FIG. 6B　　FIG. 6C

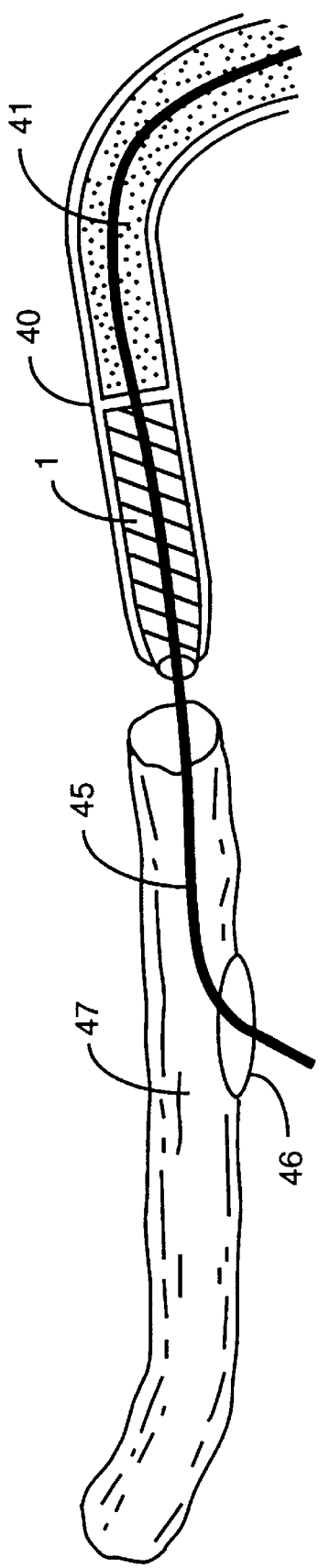
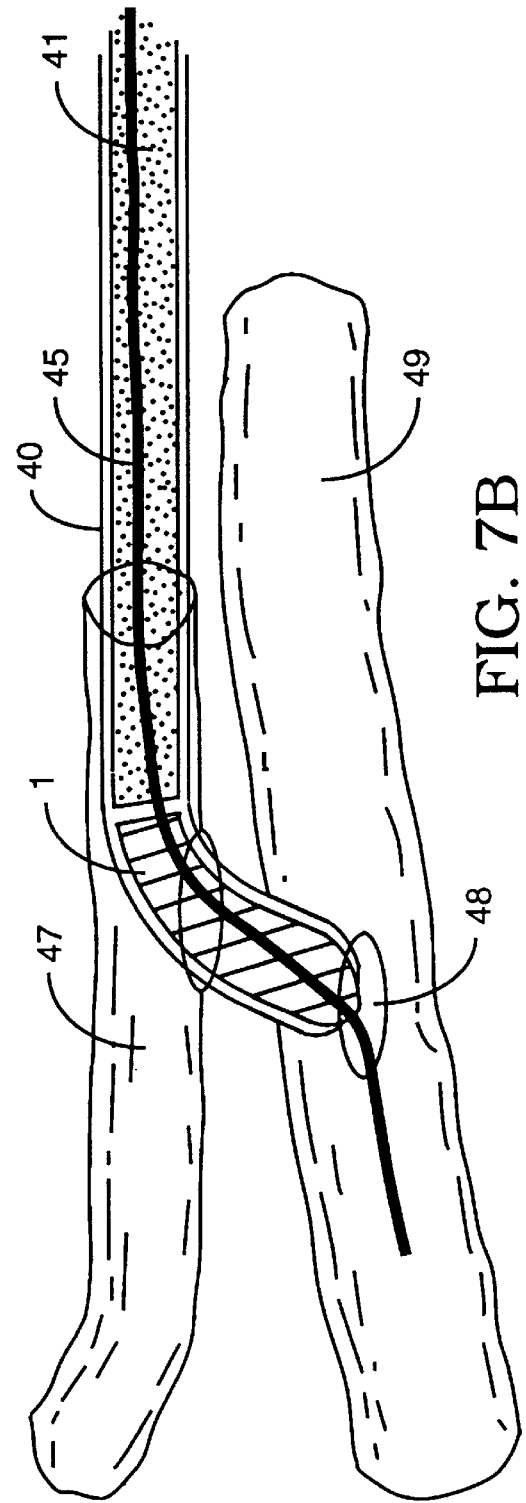
FIG. 7A
FIG. 7B

DEVICE FOR INTERCONNECTING VESSELS IN A PATIENT

TECHNICAL FIELD

This invention relates generally to the field of implantable medical devices and more particularly to such devices useful for interconnecting vessels in a patient.

BACKGROUND OF THE INVENTION

The human body has numerous vessels carrying fluid to essential tissues and areas for recirculation or excretion. When vessels become damaged, severed or wholly occluded due to physiological problems, certain sections must be bypassed to allow for the free and continuous flow of fluids. Anastomosis is performed for the purpose of connecting different conduits together to optimize or redirect flow. In cardiac surgery, anastomosis is done to bypass the occluded vessel by harvesting a portion of an unobstructed vessel and joining it to the occluded vessel below the point of stenosis.

The common procedure for performing the anastomosis during bypass surgery requires the use of very small sutures, loupes and microsurgical techniques. Surgeons must delicately sew the vessels together being careful not to suture too tight and tear the delicate tissue, thereby destroying the vessel. Long term patency of anastomosis is also an issue. Exposure of damaged vessel wall to the bloodstream can lead to formation of thrombus and possible occlusion of the artery. As cardiac surgery is moving into less invasive procedures, surgical access is being reduced, forcing surgeons to work in a constantly tighter and tighter spaces. The procedures are made more difficult due to the multiple characteristics that are unique to each anastomosis. The arteries internal diameters dimensions are hard to predict, the walls can be friable and easy to tear, often, they are covered with layers of fat, others are deeply seated in the myocardium. Cardiac surgeons sometimes inadvertently suture too loosely, resulting in leakage of fluid from the anastomosis. Leakage of fluid from the area can cause serious drop in blood pressure, acute or chronic and general changes that may endanger life or induce local scar tissue to develop and often results in further blockage or damage to the sewn vessel.

Furthermore, anastomosing blood vessels may involve risks of physical injuries to the patient. For example, when performing coronary artery bypass grafting (CABG) procedures, anastomosis often requires manipulation of the heart, so surgeons may access the back of the heart as well as the front. Patients supported by cardiopulmonary bypass during the procedure risk post-surgical complications that vary directly with the duration for which the heart is under cardioplegic arrest. In addition, surgeons performing anastomosis on a beating heart risk the possibility of a hemodynamic compromise during longer procedures. Consequently, surgeons are constantly searching for techniques to both reduce the risk of tissue damage as well as the laborious and time-consuming task of vessel suturing.

Stapling and coupling procedures have been used in performing large conduit anastomosis. While stapling is successful in gastrointestinal procedures due to the large size and durability of the vessels, it is less adequate for use in vascular anastomosis. The stapling instruments are difficult to reduce to the size required by smaller vessels like coronary arteries. When the staples are adapted to conform to the smaller sized vessels, they are difficult to maneuver and require a great deal of time, precision, and fine movement to successfully approximate the tissue. Often stapling or coupling devices requires the everting of the vessel walls. Everting may not always be practical especially for small arteries because they may tear if everted. Furthermore due to issues related to tissue capturing at the edges, the force required to trigger the stapling devices and spacing between staple points, the potential of vessel laceration or leakage from the anastomosis exists just as it does in suturing. Stapling devices also are poor at conforming to different size vessels.

BRIEF DESCRIPTION OF THE DRAWINGS

FIG. 4 includes FIGS. 4A, 4B and 4C all of which show a single alternative embodiment of the invention with FIG. 4A showing a first segment of the device in a completely folded form being inserted within an opening in a vessel, FIG. 4B showing the first segment partially unfolded and further inserted within the vessel and FIG. 4C showing the first segment completely unfolded and completely inserted within the vessel;

FIG. 5 shows an alternative embodiment of the invention where the first and second segments are connected in a manner such that each segment is at a right angle or perpendicular to the other segment;

FIG. 6 includes FIGS. 6A, 6B and 6C each of which show embodiments of the device being delivered by a surgical dispenser and inserted into a vessel with FIG. 6A showing the device almost completely inserted within the surgical dispenser lumen, FIG. 6B showing the device partially extruded from the surgical dispenser lumen and FIG. 6C showing the device completely extruded;

SUMMARY OF THE INVENTION

Figure 1:
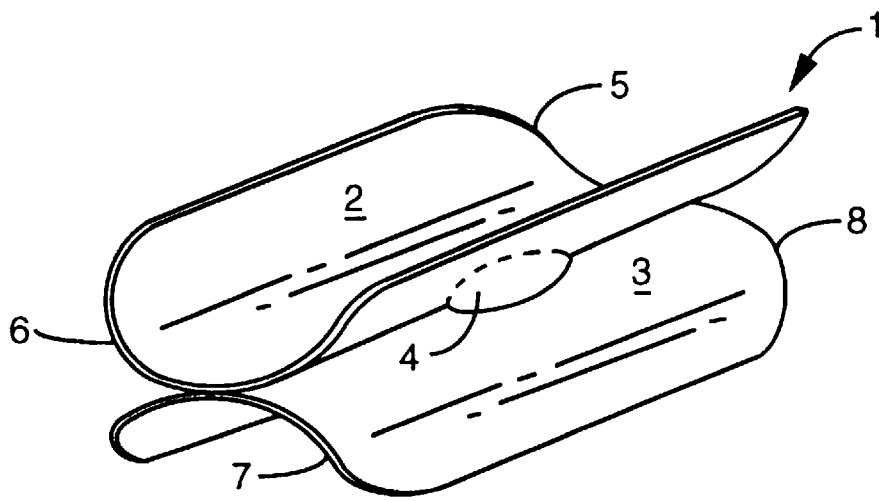
FIG. 1 is a perspective view of a simple embodiment of the invention where two partial cylindrical segments are interconnected along the periphery of an opening.

The present invention provides an implant device and an associated method for interconnecting human vessels rapidly, safely and in a minimally invasive manner. The device comprises a first segment, a second segment, and a flow opening along the periphery of the two connected segments. The first and second segments are bendable for easy insertion into an incision made within each vessel.

Upon release, each bendable segment subsequently conforms to the interior walls of a vessel to provide a sealing contact along the contact surface of the segment inserted within. The flow opening provides a permanent connection between the two segments and fluid interconnectivity between the vessels connected by the implant device. The flexible segments comprise thin-walls, thus minimally interfering with fluid flow within the interconnected vessels. The configuration of the two segments inside each vessel is such that it provides an element of force that can pull the two vessels together for a better seal and healing of artery walls. The wall pressure created by the fluid inside the vessel secures the device against the vessel wall thereby preventing leakage as well. The implant device may be made of any suitable biocompatible material including bioresorbable and biodegradable material.

The implant device may be inserted using surgical tools or alternatively using special catheter designed specifically for the placement and release of the implant device within the vessels for interconnection thereof. The implant device is preferably provided in an assortment of sizes, shapes, configurations, etc. in order to interconnect vessels of various sizes, shapes and orientations.

The implanted device, and the associated implant method, is particularly applicable for performing anastomosis surgery for grafting two juxtaposed cardiac vessels. The cardiac anastomosis surgery may be performed on either a stopped or a beating heart.

An object of the invention is to provide a device for interconnecting two vessels within a patient—which device is configured so as to be easily inserted into an opening in a vessel and allow for a flow of material through the vessel after insertion.

Another object of the invention is to provide for a method of quickly and efficiently performing an anastomosis.

An advantage of the invention is that the method can be readily performed because the device is small, flexible and easily manipulated.

A feature of the invention is that is can be comprised of a variety of materials.

Another feature of the invention is that the device is flexible and matches the compliance of the native vessels to minimize irritation to the endothelial cells of the vessel wall.

Another feature of the device is that surface contact area of the device to the vessel wall is minimized to reduce unwanted biological responses to the implant.

Another feature of the invention is that one device can be used to accommodate a wide range of different size vessels.

Another feature of the invention is that the device can be sold as a kit containing a range of different sizes of devices that could be useful for insertion into a wider range of vessel sizes.

An aspect of the invention is a device comprised of a first segment connected to a second segment along the periphery of an interconnecting opening. Another aspect of the invention is that the device can be loaded into a catheter delivery system.

Another aspect of the invention is that the device can be loaded in a surgical delivery dispenser.

Another aspect of the invention is that it facilitates the application of adhesive.

Another aspect of the invention is that it can be inserted using robotic assist devices (U.S. Pat. No. 5,855,583).

Another aspect of the invention is that it can be used with a variety of conduits, vascular grafts, artificial or prosthetic.

Examples of vascular grafts are coronary artery to the coronary vein, radial artery to the coronary artery, saphenous vein to the coronary artery, gastroepoploic artery to the coronary arteries, femoro-popletial bypass using vein or other conduit, etc.

Yet another aspect of the invention is that the anastomosis procedure can be carried out using a loading device or an endovascular catheter in order to insert a device of the invention.

These and other objects, aspects, advantages and features of the invention will become apparent to those skilled in the art upon reading this disclosure in combination with the accompanying figures.

DETAILED DESCRIPTION OF THE PREFERRED EMBODIMENT

Before the present, devices and methods used therein are disclosed and described, it is to be understood that this invention is not limited to particular components, devices or steps as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

Figure 2:
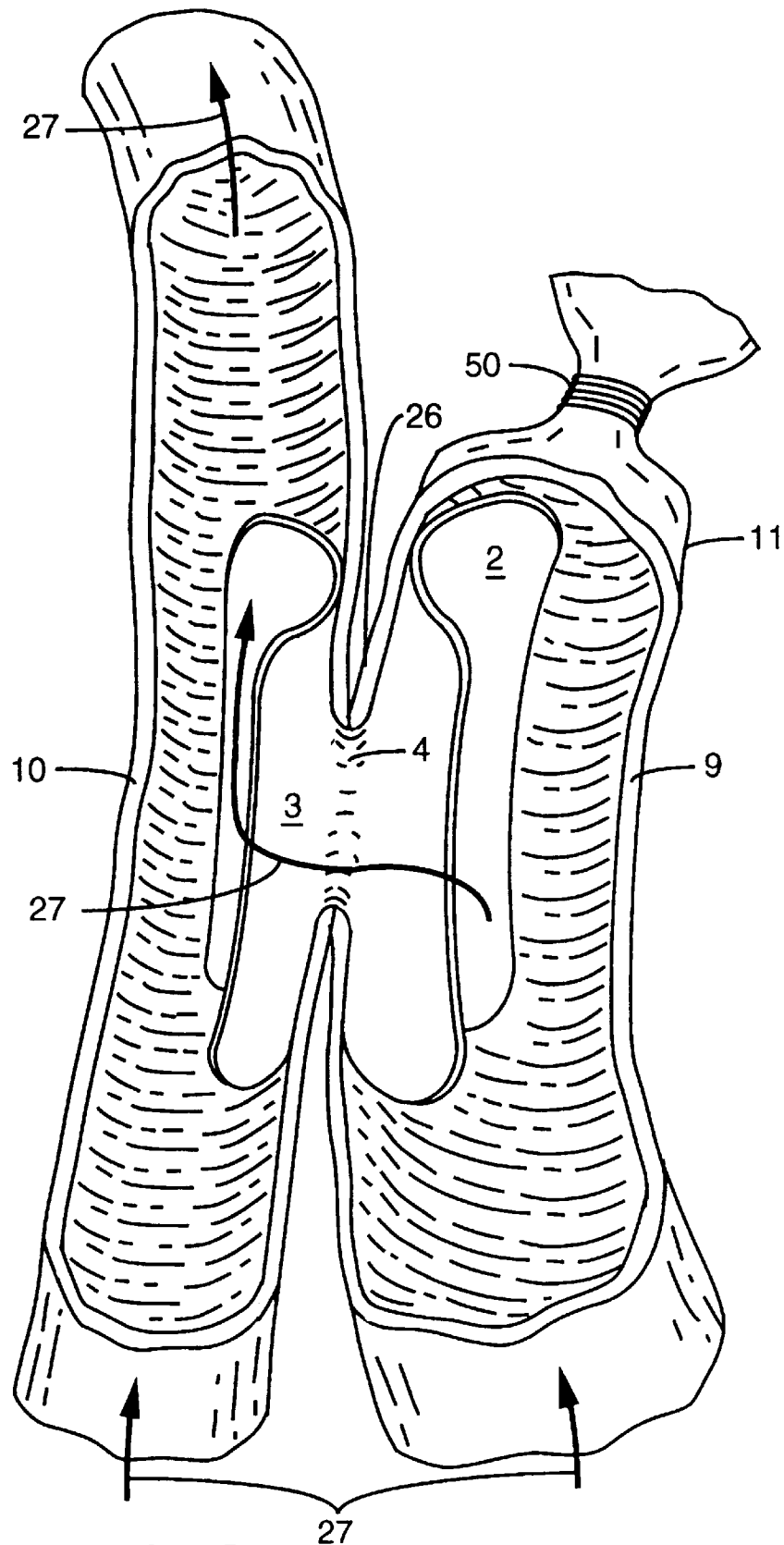
FIG. 2 shows the embodiment of FIG. 1 inserted within two vessels thereby interconnecting those vessels.

FIG. 1 shows the flexible device 1 that is comprised of a first segment 2 and a second segment 3. In this embodiment the first segment 2 and the second segment 3 are mirror images of each other and are interconnected (preferably in a permanent manner) to each other along the periphery of an interconnecting opening 4. The first segment 2 has an end 5 and an opposite end 6. The ends 5 and 6 are equal distance from the center of the opening 4. Although the ends shown here have smooth, rounded edges the ends may be shaped in any desired form noting that it is preferable to have end edges which can be easily inserted into a vessel and not cause damage to the vessel. The second segment 3 has an end 7 and an opposite end 8 each of which are also equal distance from the center of the opening 4. The device 1 as shown in FIG. 1 is shown inserted into vessels 9 and 10 in FIG. 2. Depending on the particular configuration of the device 1 the insertion can be carried out in a number of different ways. As an example, the first segment 2 can be constricted so that it forms a tighter semi-circle and/or the ends 5 and 6 can be folded towards each other. In this position the ends 5 and 6 can be made to touch each other and can be inserted within the opening of a first vessel 9. Thereafter the second segment 3 can be inserted within an opening of a second vessel 10 in the same manner. When the first segment 2 and second segment 3 are released from their constricted state they expand and conform to the interior wall of the respective vessels 9 and 10, thereby interconnecting these vessels via the center of the opening 4. Thus, a side-to-side interconnection of vessels 9 and 10 is completed. In many situations it is desirable to close off one end of one of the vessels. As shown in FIG. 2 the end 11 of the vessel 9 has been tied off.

In the embodiment of the device 1 as shown in FIG. 1 the first segment 2 and second segment 3 are mirror images. However, the two segments can be different in size (circumference, width or length) from each other. Different sizes are useful in situations where it is desirable to interconnect two vessels which are different in size. The embodiment of FIG. 1 also shows that the ends 5 and 6 of the first segment 2 as well as the ends 7 and 8 of the second segment 3 are equal distance along their entire edge from the center of the opening 4. However, the ends 5, 6, 7 and 8 can be configured in any given manner and distance from interconnection hole 4 as well as being tapered or rounded on each or either end.

FIG. 2 illustrates an exemplary anastomosis surgery consists of grafting two juxtaposed vessels 9 and 10. The surgeon inserts one segment 2 in one vessel 9 and the other segment 3 into the other vessel 10 whereby the gentle pressure created by device 1 due to its expansion prevents leakage of fluid from the graft site 26. The fluid then passes along flow path 27 from vessel 9 through the hollow connecting hole 4 into the vessel 10. The surgeon may tie off the distal end of the graft vessel using a thread 50, staple or other suitable closure or binding means. When the segments 2,3 expand back to their original size and shape, they will conform to the vessel walls to provide gentle pressure and a firm fit.

After insertion and completion of the anastomosis using the device 1 shown in FIG. 1 and inserted within FIG. 2, it is necessary that the free end of the vessel be tied off by any standard closure or binding means using sutures, metal clips or other securing mechanisms such as the thread 50 shown in FIG. 2. For example, the saphenous vein, right or left internal mammary artery, or radial artery used to form the anastomosis is terminated or closed off at the end as shown with the thread 50. Other closure means are taught in U.S. Pat. No. 5,234,448. Closing off of the vessel 9 would clearly not be necessary during any side-to-side anastomosis where the vessel is to be anastomosed to another vessel at a more distant point. During the procedure, the placement of stay sutures in order to stabilize the graft to the heart or to juxtaposition the two vessels together may be required. Such sutures are easily placed through the fat or tissue surrounding the vessels in order to provide additional stability to the anastomosis. This is normally performed when grafting an internal mammary artery to the coronaries but may be required for the anastomosis using this device in order to prevent the two vessels from being inadvertently separated from each other during or after the procedure.

Although the device 1 shows a first segment 2 and second segment 3 each of which has a partial cylindrical shape and each of which is identical in size and shape to the other, a variety of different configurations are contemplated by the present invention. Some of these configurations are shown in the other embodiments—see FIGS. 3, 4 and 5. However, those skilled in the art will contemplate numerous additional embodiments upon reading this disclosure. As one example it is pointed out that the first segment 2 and second segment 3 can be flat, i.e. have outer surfaces which are contained within a single plane. If each segment is flat then the segment is folded before being placed in the opening of a vessel. Once in place each segment will assume the configuration of the interior wall of the vessel it is placed within. Further, each segment will apply some pressure against the interior wall of the vessel thereby holding the device in place. With each of the embodiments of the invention, it is preferable for each of the segments to have flexibility and be in a slightly bent or constricted shape when present within the interior wall of the vessel so that the outer surface of each segment is forcing itself against the interior wall of the vessel while the device is attempting to reassume its original configuration. The device is also held in place, to some degree, by blood pressure or other fluid pressure within the vessels forcing against the device.

In the device 1 shown in FIG. 1 and used within FIG. 2, the first segment 2 and second segment 3 are connected along the periphery of the opening 4. Accordingly, the first segment 2 and second segment 3 touch each other along a line extending outwardly along the periphery of the opening 4 to the respective ends of each segment. However, in an alternative embodiment (not shown), the opening 4 can be in the form of an open channel which could be cylindrical in shape. The open channel would connect to the opening 4 on each segment of the device. The channel would separate the first segment 2 from the second segment 3 by the length of the channel and it would be used in situations where the vessels being connected are not positionable against each other. For example, one of the vessels may be embedded within a layer of muscle or other tissue.

Figure 3:
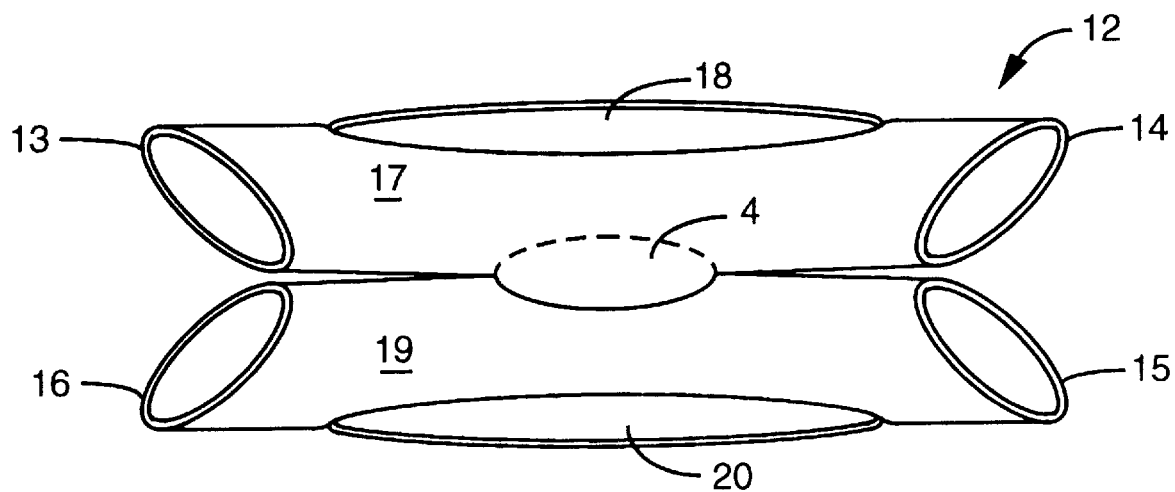
FIG. 3 shows an alternative embodiment of the device of the invention where full (complete) cylindrical segments having tapered ends are interconnected along the periphery of an opening wherein each of the segments has an opening in its upper surface.

FIG. 3 shows an alternative embodiment 12 of the invented device having tubular segments 17 and 19. Tubular segments 17 comprises tapered end 13 and 14 and tubular segment 19 comprises tapered ends 15 and 16. The tapering of these ends may have a low friction coating and be very smooth thereby providing a number of advantages which include making it easier to insert the end into a vessel. The configuration of FIG. 1 shows that the first segment and second segment are each configured in the form of a portion of a cylinder. However, the device could be configured so that each segment is a complete cylinder (see FIG. 3). An advantage of having each of the segments a partial cylinder is the ability to conform to a wider range of different vessel diameters to improve the fitting range. Another advantage is the maximizing of the amount of endothelial wall of the vessel not covered by the device 12 to promote healing and minimization of the cell response to the implantable device 12. In the configuration shown in FIG. 3 a complete cylinder is provided for each segment. However, the first segment 17 has an opening 18 in its upper surface and the second segment 19 has an opening 20 in its upper surface.

Another embodiment of the invention is shown in FIGS. 4A, 4B and 4C each of which shows a folding/expandable device 21. In FIG. 4A the segment 22 is in its expanded configuration and the segment 23 is in a completely folded configuration. FIG. 4A shows the segment 23 being inserted into an opening 24 in a vessel 25. Once the segment 23 has been inserted it is released and it begins expanding to a partially folded configuration as shown in FIG. 4B. FIG. 4C shows the segment 23 completely expanded. After this procedure is completed the same procedure could be carried out with the segment 22 on a separate vessel (not shown).

In the device 1 as shown in FIG. 1 the first segment 2 and the second segment 3 are connected in a manner such that they are parallel to each other. However, as shown in FIG. 5 the first segment 30 may be positioned at a right angle to the second segment 31. As with the embodiment as shown in FIG. 1 the device 33 shown in FIG. 5 has the segments 30 and 31 interconnected along the periphery of an opening 4. Those skilled in the art will recognize that the segments of the device can be interconnected at other places. However, interconnection in some manner along or near the periphery of the opening is important in order to provide a seal between the first and second segments. The device 33 shown in FIG. 5 is also different from the device 1 shown in FIG. 1 in that the first segment 30 is larger in diameter than the second segment 31. This differentiation in the diameter of the two segments is preferable in situations where the surgeon is interconnecting two vessels which are different in diameter.

In the embodiment as shown in FIG. 5 the first segment 30 and second segment 31 are positioned at a 90° angle with respect to each other. However, the first and second segments can be positioned at any angle relative to each other, i.e. any angle between being directly parallel as shown in FIG. 1 to being at a right angle or 90° angle as shown in FIG. 5. Thus, the embodiment of FIG. 1 shows the first segment 2 and second segment 3 positioned at a 0° angle. In this position it is sometimes difficult to provide the necessary access in terms of a required line of sight or manual manipulations. Accordingly, offsetting one segment relative to the other at some angle (between 0° to 90° or more preferably 30° to 90°) visual and manual access are improved. In the embodiment of FIG. 5 the first segment 30 and second segment 31 are directly connected to each other along the periphery of the opening 4. However, as explained above with respect to the embodiment of FIG. 1 the first and second segments can be interconnected by a channel. The channel could be of any length but is preferably 1 cm or less in length and has a diameter which is substantially equal to the diameter of the interior wall of one or both of the vessels being connected.

The device 33 shown in FIG. 5 is also different from the prior configuration shown in FIG. 1 in another important feature. Specifically, the larger first tubular segment 30 nearly forms a complete cylinder. The edges 34 and 35 are close to each other compared to those of the device shown in the configuration of FIG. 1, which forms half or less than half of a cylinder. The second tubular segment 31 (FIG. 5) is shown in a state where it initially forms a complete cylinder along a separation string or thread 37 (shown along the dashed line 36). When thread 37 is pulled the edges of the second tubular segment 31 separate causing the tubular segment to form a partial cylinder as is shown with the first tubular segment 30. Thus, the second tubular segment 31 is shown in its original state wherein the first tubular segment 30 is shown in a state after the separation thread 37 has been pulled apart. Once the separation thread 37 has been pulled apart and the edges are separated from each other, the cylinder expands radially outwardly to conform to the interior walls of the vessel. Thus, the device is first inserted into the vessels and then the separation thread 37 in each tubular segment is pulled apart allowing the edges to separate and the partial cylinder to expand and apply force against the interior walls of the vessel. In this manner the device is securely held in place and the fluid flow within the vessel is not obstructed by the device.

In describing the device of the present invention the terminology "conforms" or "conforms to" and the like is used to refer to the outer surface area of each segment of the device. What is intended by this terminology is that the device is designed to sufficiently conform and seal the interior walls of the vessel when it is placed within. As indicated above each segment of the device may be planar in configuration and bent into a curved cylindrical portion during insertion into a vessel. Once the segment is inserted and released, and the segment attempts to resume its original configuration and by doing so it conforms substantially to the interior walls of the vessel.

The embodiment shown in FIG. 5 shows the application of a thread 37 for separating the edges of a tubular segment and conforming to the interior walls of the vessel. Other embodiments edge separation and conforming embodiments of the invention are possible. For example, both segments or portions of the device shown in FIG. 5 could be separated providing edges such as the edges 34 and 35 shown in the first segment 30. A thread could be tied around the first segment 30 forcing the edges 34 and 35 together or even forcing them to overlap each other. Thereafter the segment 30 is placed within the vessel and the thread is removed. After the thread is removed the segment 30 attempts to resume its original configuration and the outer surfaces of the segment 30 force themselves against the inner surfaces of the vessel and thereby conform to the interior wall of the vessel. Other means of constricting the diameter of each segment or portion prior to insertion and thereafter allowing that segment or portion to relax and attempt to reassume its original configuration are contemplated by the present invention.

MATERIAL

The materials used may be bioresrobable, such as degradable hydrogels, lactides/glycolides or PHAs. A metal mesh with the appropriate geometrical features, sinusoidal and circular, and cross patterns to provide adequate flexibility may be appropriate in certain circumstances; nitinol (a super elastic nickel titanium alloy) or stainless steel can be used. Non resorbable polymers and elastomers such as silicones, fluoropolymers, polyolephins or polyurethanes might also be used.

Those skilled in the art will recognize that certain materials are preferred in connection with certain uses of the invention. In general the material should be comprised of one or more compounds which are biocompatible and nontoxic to the vessels into which they are inserted. In general the device is used for connecting vessels of the cardiovascular system and therefore should be comprised of a material which provides a high degree of hemocompatibility. The material should not prevent growth of a new intima layer. The material used in the construction of the invented device should be designed to have thickness and properties appropriate for the stiffness and flexibility of the vessel into which the device is inserted. It should be noted that artery walls continuously dilate and contract due to the systole and diastole of the heart. If the device is too rigid the device can cause irritation and injury to the intima layer of the vessel. Accordingly, the device should be designed to avoid any inflammatory response or immune response that has adverse consequences. In addition to having the desired degree of flexibility and composition the device should be designed so that it does not present protrusions or disruptions to the flow of material through the vessels which are being connected by the device. Interruption of flow can cause clots to form which could in certain circumstances be fatal to the patient.

In a preferred embodiment the device of the invention is bioresorbable material and it may be comprised of all or any of the following materials: Collagen, Polycaprolactone, Poly (glycolic acid), PLLA, Poly(3-hydroxybutric acid), Poly(dl-lactic acid), Poly(1-lactic acid), Poly(dl-lactide/glycolide) 50:50, Poly(hydroxyvalerate), Poly(hydroxyvarelate-co-hydroxybutyrate), or other PHAs. Further, see the materials disclosed and described in U.S. Pat. No. 5,056,211 as well as patents and publications cited therein.

It is also possible to produce a device which is comprised of metal or has a metal mesh substructure coated with a polymer or bioabsorbable material. When the device is comprised of metal or includes metal components the metal must be sufficiently flexible to provide the desired degree of flexibility in the vessels it is used in. The geometric pattern of the metal within the device may be important to obtaining preferred results and may be a sinusoidal or circular metal substructure. The device may be comprised of surgical grade stainless steel or nitinol which has useful superelastic properties. Polymers may be used not only to coat metals but to produce the entire device. Non resorbable polymers and eslastomer materials such as silicone or fluropolymers can be produced in the desired size, shape and flexibility.

Any or all of the different materials can be coated with a desired compound or drug. The device blood contacting surface may be lined with endothelial cells. These cells may be cells extracted from the patient the device is being placed in or from a tissue culture of such cells from another patient. Further, the materials may be embedded with any desired compound or drug which provides desired properties to the device. Useful coatings include drugs such as heparin which may be used alone or in combination with hydrogels or hydrophilic compounds. Any anticoagulant compound may be extremely useful as a coating on devices inserted into the vessels of the cardiovascular system. Compounds such as Taxol may be a useful compound for coating or embedding within materials of a device of the invention.

A device of the invention may be comprised of any material that is appropriate for localized delivery of various compounds including compounds such as antiplatelet agents, calcium agonists, antiinflammatory compounds, antiproleferative drugs, hypollpidemic agents, and angiogenic factors. The device may be comprised such that all or any of these compounds are coated on the surface of the material, embedded within it or incorporated within a chamber (not shown) of the device so that the compound is released in a metered fashion from the device to the area surrounding the anastomosis.

DELIVERY SHEATHS

The device of the invention in any of its embodiments may be inserted without the use of special surgical tools. Specifically, the device may be inserted using the surgeon's fingers alone or in combination with other surgical equipment normally used when operating on a patient. In certain situations it may be desirable to provide the device of the invention using a catheter or surgical dispenser through which the device is moved and inserted. FIG. 6 which includes FIGS. 6A, 6B and 6C is a simple representation of how the device can be inserted using a surgical dispenser for bypass surgery with direct access to the heart.

The device such as the device shown in FIGS. 1, 3 or 5 as well as any alternative embodiment of these will be referred to as the device 1 as shown in FIG. 6A. The device 1 is placed within the delivery sheath 40. Because the device is flexible, it can be compacted to a relatively small shape. After being placed in the delivery sheath 40, the push plunger 41 is used to force the device 1 through the delivery sheath 40. The end 42 of the delivery sheath 40 is preferably first placed within an opening of a vessel. After being placed in that opening the push plunger 41 is used to force the first segment 2 of the device 1 out of the delivery sheath 40 as shown in FIG. 6B. Thereafter, the end 42 of the device is withdrawn from the opening, of the first vessel and placed in the vicinity of an opening of a second vessel. At this point, the plunger 41 is forced forward until the second segment 3 of the device 1 is extruded from the delivery sheath 40. The surgeon may ease the insertion by manipulating the vessels and the device 1 for optimum placement. At this point, the device 1 is in place interconnecting two vessels (See FIG. 2).

Figure 7C:
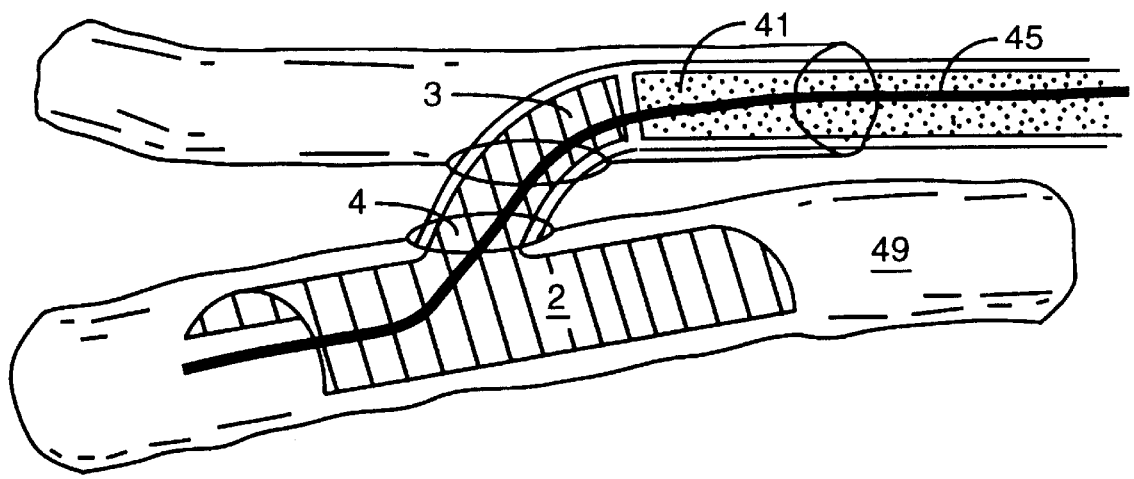
FIG. 7 includes FIGS. 7A, 7B, 7C, 7D and 7E each of which show a step of an alternative embodiment of putting the device of the invention in place using a catheter and guidewire with FIG. 7A showing the device within the catheter and a guidewire in place, FIG. 7B showing the device moved toward the opening in the vessel guided by the guidewire, FIG. 7C showing the device partially inserted, FIG. 7D showing the device completely inserted into two vessels thereby interconnecting those vessels and FIG. 7E showing the catheter withdrawn.
Figure 7D:
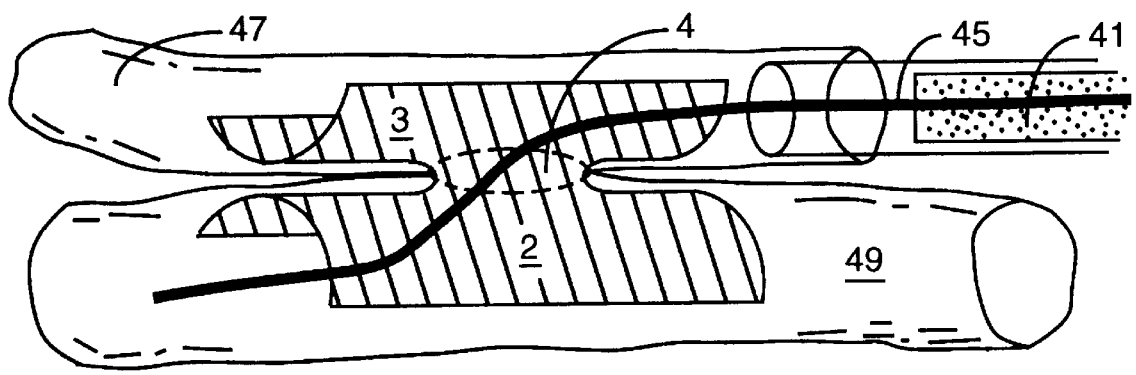
Figure 7E:
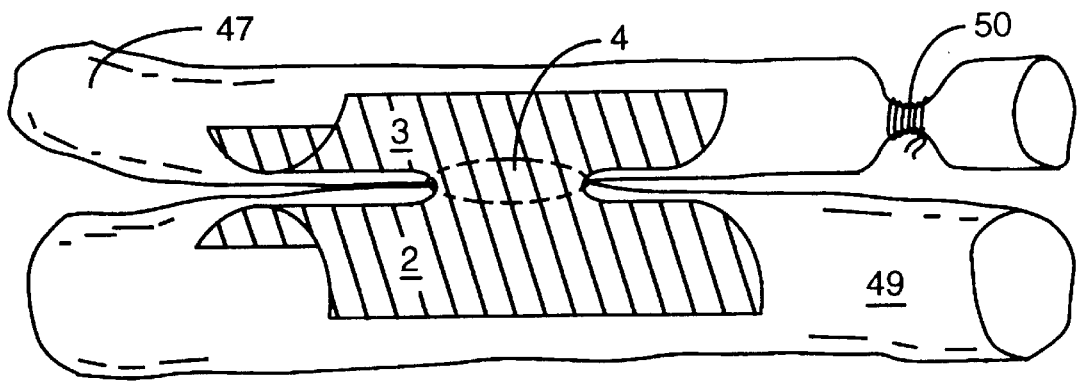

For a less invasive approach, a catheter and a guidewire delivery system can be used as is shown in FIGS. 7A, 7B, 7C, 7D and 7E. The device 1 is delivered by the catheter through the graft vessel 47. In this embodiment the device 1 is placed within the delivery sheath 40 in a manner such that guidewire 45 is led through the opening 4 (see FIG. 1) of the device. The guidewire 45 is then inserted within an opening 46 of a graft vessel 47. At this point, the push plunger 41 is used to force the device 1 forward toward the opening 46 as is shown in FIG. 7B. The guidewire then leads the catheter into an opening 48 of a native native vessel 49 as shown in FIG. 7B. The device 1 as shown in FIG. 7B is now in position for insertion into the opening 48 of the native vessel 49. The push plunger 41 is then moved forward as shown in FIG. 7C. This causes the first segment 2 of the device 1 to be inserted into the opening 48 of the native vessel 49. Upon being inserted into opening 48, the first segment 2 expands into its original shape. When this is completed, the delivery sheath 40 is positioned relative to the opening 46 of the graft vessel 47 and the push plunger 41 is moved forward to force the second segment 3 of the device 1 out of the delivery sheath 40. The second segment 3 also expands into its original shape upon being forced out of the delivery sheath 40. When this is accomplished the result is shown in FIG. 7D. At this point the device 1 is completely inserted and the vessels 47 and 49 are interconnected by the 14 opening 4 of the device 1. Thereafter the delivery sheath 40, push plunger 41 and guidewire 45 may be withdrawn completely from the patient.

One aspect of the invention is a device such as the device 1 of FIG. 1 or device 33 of FIG. 5 loaded into a catheter delivery system of the type shown in FIGS. 7A–7E. The device 1 is loaded into the delivery sheath 40 so that the guidewire 45 goes through the opening 4. The combination of the device 1 and delivery sheath 40 can be conveniently sold as a unit for performing an anastomosis. Such a combination product provides the surgeon with a device properly matched in size with an insertion catheter.

Figure 8A:
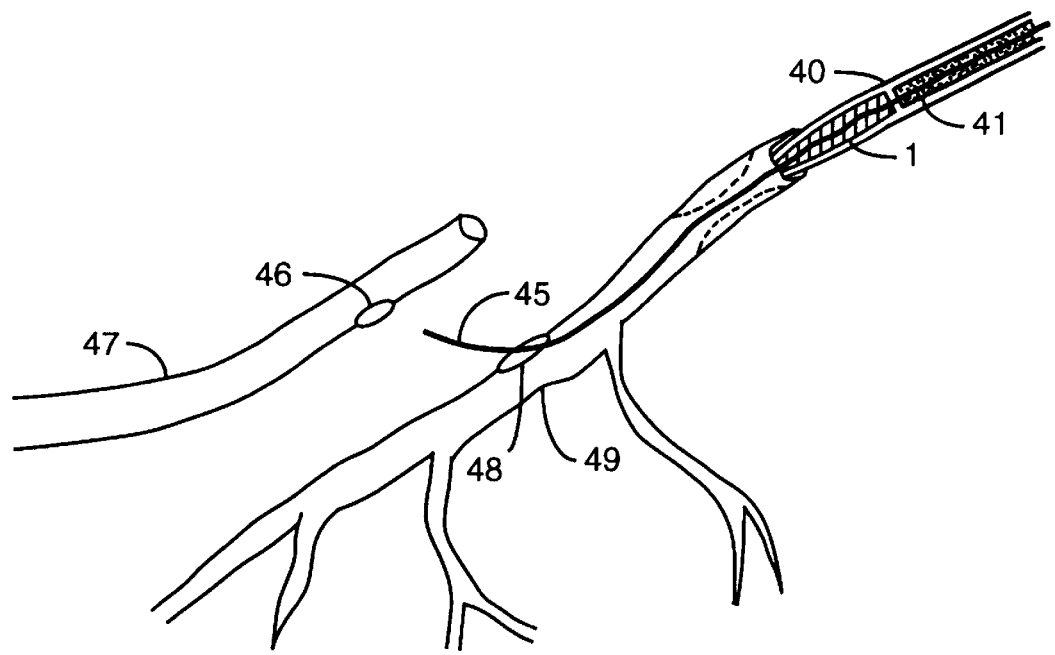
FIG. 8 includes FIGS. 8A, 8B and 8C which show three steps of a device of the type shown in FIG. 1 being inserted into and interconnecting two vessels with FIG. 8A showing the device in the catheter, FIG. 8B showing the guidewire inserted in the vessel opening and FIG. 8C showing the device in place.
Figure 8B:
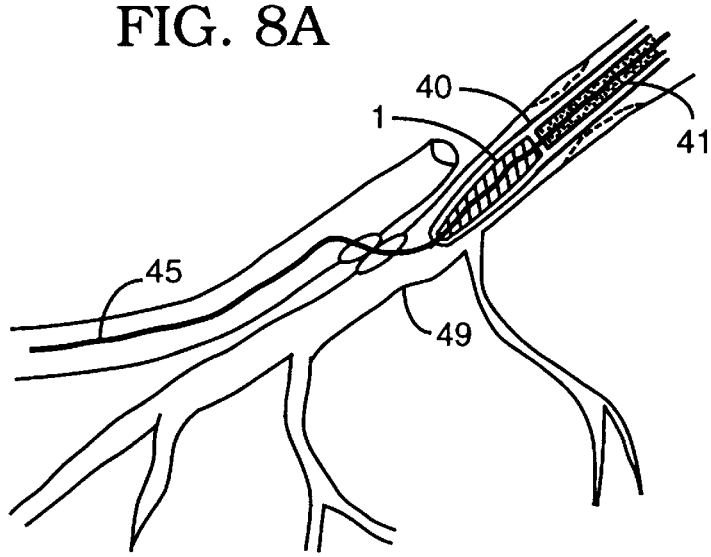
Figure 8C:
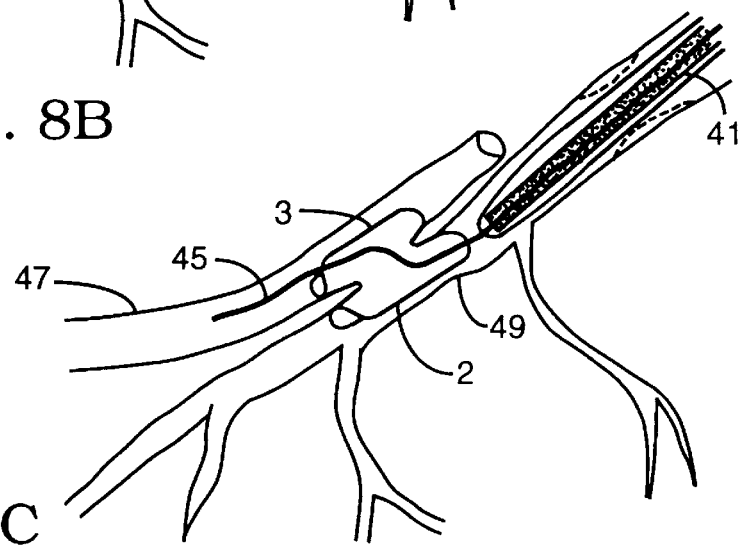

Another embodiment of the catheter insertion procedure is shown in FIGS. 8A, 8B and 8C. In this embodiment the device 1 is delivered using a catheter through the native vessel 49. Specifically, the delivery sheath 40 has the device 1 loaded within it. The device 1 is loaded into the delivery sheath 40 in a manner such that the guidewire 45 goes through the opening 4 of the device 1 . Further, the push plunger 41 is positioned within the delivery sheath 40. The end of the delivery sheath 40 is placed within the native vessel 49 and the guidewire 45 is moved through the native vessel 49 and out of the opening 48 of the native vessel 49 as shown within FIG. 8A. Thereafter, the catheter is moved forward and the guidewire 45 is moved into the opening 46 of the graft vessel 47 (see FIG. 8B). Thereafter, the push plunger 41 is moved forward so that the device 1 forced out of the catheter 40. The first segment 3 of the device 1 enters the opening 46 of the graft vessel 47 and the second segment 2 of the device 1 remains within the native vessel 49 (see FIG. 8C).

After insertion and completion of the anastomosis the free end of the vessel 47 is tied off in a manner as shown within FIG. 2. It may be necessary to further expand the device by the use of a balloon catheter not very differently than a post dilatation of an angioplasty stent. This may help fully expand the device and enhance the sealing and connecting properties of the device. It may also be necessary to utilize stay sutures to stabilize the graft near the heart. These sutures are placed through fat or tissue surrounding the vessel in order to provide additional stability to the anastomosis. This is normally done when grafting the internal mammary artery to the coronaries but may be necessary for all anastomosis using this device in order to prevent the vessels 49 and 47 from being inadvertently separated from each other.

STOPPED HEART/BEATING HEART

The device of the present invention can be used to interconnect vessels or more specifically complete an anastomosis while the patient's heart is beating or after the patient's heart has been stopped. Beating heart procedures can be carried out by making a variety of different types of initial incisions which could include a sternotomy where the patient's sternum is bisected or by making smaller incisions and utilizing minimally invasive surgical devices and methods (see Benetti, F. in U.S. Pat. No. 5,888,247). After the necessary incisions are made the heart is stabilized using a stabilizer device. Thereafter the device of the invention is inserted by one or more different means described herein. Specifically, the first segment of a flexible device is inserted by bending the device and moving it into an opening in a first vessel. After bending the device and inserting it within the vessel it is released and the first segment of the device resumes its original configuration where the device conforms to an inner circumference of the first vessel. The first segment of the device includes an opening and is connected to a second segment of the device along the periphery of that opening. The second segment of the device is then bent and moved into an opening of a second vessel. Thereafter the device is released and it resumes its original configuration and conforms to the interior wall of the second vessel.

The device can also be used in a stopped heart situation. Many of the different types of initial incisions mentioned above or others can be used to access the patient's chest cavity. A suitable graft vessel is harvested from the patient. Thereafter the patient's heart is stopped using a suitable cardioplegia. Thereafter, the steps referred to above with respect to insertion of the device are carried out. Although the present invention can be used in connection with a stopped heart procedure one of the advantages of the present invention is the ease of manipulation of the device in order to carry out an anastomosis. Because of the simple efficient manner in which the device of the invention can be manipulated and inserted it can generally be carried out while the patient's heart is beating.

ROBOTIC ASSIST INTERVENTION

The device can be used when robotic assist device are utilized by the surgical staff. Robotic assist device surgery is typically performed by the surgeon through the use of robotic arms. The use of the robotic arms scales the motion of the surgeon and filters out unwanted tremors. This allows the surgeons to perform the surgery through smaller incisions and in more constricted spaces. Examples of such systems are the ones marketed by Intuitive Surgical Systems as described in U.S. Pat. No. 5,855,583.

SURGICAL ACCESS AND VISUALIZATION

The device and the catheter delivery systems can be used during hybrid procedures where surgical procedures are combined with interventional cardiology techniques. Such procedure use fluoroscopy to visualize and position the catheter delivery systems. The catheter is normally placed through femoral or radial access. Direct surgical access to the heart is typically achieved via small incisions in the chest or abdomen. A single or multiple trocar ports or a minimally invasive small retractor is placed in these incisions. An endoscope may be used to aid in visualization.

The device can also be used in complete percutaneous procedures where no direct access to the heart is available to the physicians.

STABILIZING DEVICE IMPLANTATION

Each embodiment of the invention is designed in a manner such that it does not require additional devices, sutures, staples or other materials to hold the device in place. Preferably, the first and second segments of the device are joined and configured in a manner such that once the device is in place the segments will apply sufficient force against the interior walls of the vessel to securely hold the device in place. Furthermore, fluids flowing through the vessels may provide additional stabilizing force for securing the device in place within the vessel. After the device has been held in place for significant periods of time, the vessels will naturally develop a new intimal layer and fuse. At this point the device may no longer be needed and could, if so designed, begin dissolving.

In certain embodiments and certain situations it may be desirable to add additional means of holding the device in place. However, the additional means preferably include a biocompatible glue. The glue could be applied after the device is implanted or placed on the device prior to implantation. Any biocompatible glue could also include other drugs such as growth factors that would aid in causing the vessels to grow together in the desired manner. The instant invention is shown and described herein in what is considered to be the most practical, and preferred embodiments. It is recognized, however, that departures may be made therefrom, which are within the scope of the invention, and that obvious modifications will occur to one skilled in the art upon reading this disclosure.

What is claimed is:

1. A flexible device for performing an anastomosis, comprising:

a first portion having a flexible surface which conforms to an inner surface of a first conduit of a patient in a sealing manner; and a second portion having a flexible surface which conforms to an inner surface of a second conduit of the patient in a sealing manner;

wherein the first portion is permanently connected to the second portion along a periphery of an opening in the first portion and the second portion, wherein the first portion and the second portion are flexibly bendable for inserting into the first and second conduits.

2. The device of claim 1, wherein the first portion has a cylindrical shape.

3. The device of claim 2, wherein the first portion has a first edge and a second edge, the first edge and a second edge are connected together by a removable binding means such that the first portion has a cylindrical shape and such that the first portion is contracted into a smaller size compared to its size when the binding means is removed.

4. The device of claim 1, wherein the first portion has a substantially planar shape.

5. The device of claim 1, wherein the first portion and the second portion are aligned substantially parallel to each other along the longitudinal axes of the first portion and second portion.

6. The device of claim 1, wherein the first portion is aligned at an angle relative to the second portion along the longitudinal axes of the first portion and the second portion.

7. The device of claim 1, wherein the device is comprised of a flexible metal material.

8. The device of claim 1, wherein the device is comprised of a bioresorbable material.

9. The device of claim 1, wherein the device is comprised of a polymer material.

10. The device of claim 1, wherein the device is coated on at least one surface with a medication material selected from a group including anti-platelet agents, calcicum agonists, anti-inflammatory, anti-proleferative drugs, hypollpidemic agents, anti-coagulent agents, endothelial cells, and angiogentic factors.

11. The device of claim 1, wherein the device is comprised of medication selected from a group including anti-platelet agents, calcicum agonists, anti-inflammatory, anti-proleferative drugs, hypollpidemic agents, anti-coagulent agents, endothelial cells, and angiogentic factors.

12. The device of claim 1, further comprising a a biocompatible glue coated on a surface of the device for providing additional stability when attaching the device to the first and second conduits.

13. The device of claim 1, wherein the first portion and the second portions are substantially similar in size and shape.

14. The device of claim 1, wherein the first portion and second portions are different in size and shape.

15. A system for performing an anastomosis, comprising:
    a delivery catheter comprising:
        a catheter tubing;
        a push plunger positioned coaxially in the catheter tubing, wherein the plunger is moveable in a manner so as to push material out of the catheter; and
        a guidewire positioned coaxially in the catheter tubing;
    an anastomosis device comprising:
        a first portion having a flexible surface which conforms to an inner surface of a first conduit of a patient in a sealing manner; and
        a second portion having a flexible surface which conforms to an inner surface of a second conduit of the patient in a sealing manner;
        wherein the first portion is connected to the second portion along a periphery of an opening in a first portion and the second portion;
        wherein the anastomosis device is compressible to a smaller size relative to an original size for inserting into the catheter tubing, and is expandable to the original size so that the first and second portions conform to the inner surfaces of the first conduit and the second conduit.

16. The system according to claim 15, wherein said system further comprises a stabilization means for maintaining the position of said device following implantation.

17. A loaded delivery catheter for guiding and positioning a flexible anastomosis device into conduits of a patient, the delivery catheter comprising:
    a catheter tubing;
        a push plunger positioned coaxially in the catheter tubing, wherein the plunger is moveable in a manner so as to push material out of the catheter;
        a guidewire positioned coaxially in the catheter tubing; and
        a flexible anastomosis device according to claim I positioned in the catheter tubing.

18. The system of claim 17, further comprising a biocompatible glue.

19. A method of interconnecting conduits in a patient using a flexible anastomosis device having a first portion connecting to a second portion along a periphery of an opening in the first portion and the second portion, comprising the steps of:
    bending a flexible first portion of the flexible anastomosis device to a reduced size, the first portion having a flexible surface which conforms to an inner surface of a first conduit of a patient in a sealing manner;
    inserting the bent first portion into an opening of the first vessel, wherein upon being inserted into the first conduit, the bent first portion expands conforming to the inner surface of the first conduit;
    bending a flexible second portion of the flexible anastomosis device to a reduced size, the second portion having a flexible surface which conforms to an inner surface of a second conduit of a patient in a sealing manner; and
    inserting the bent second portion into an opening of the second conduit, wherein upon being inserted into the second conduit, the bent second portion expands conforming to the inner surface of the second conduit.

20. The method according to claim 19, wherein said method further comprising stabilizing said implanted device with a stabilization means.

* * * * *

UNITED STATES PATENT AND TRADEMARK OFFICE
CERTIFICATE OF CORRECTION

PATENT NO.    : 6,251,116 B1
DATED         : June 26, 2001
INVENTOR(S)   : Hani Shennib et al.

It is certified that error appears in the above-identified patent and that said Letters Patent is hereby corrected as shown below:

<u>Column 13</u>,
Line 14, change "calciicum" to -- calcium --;
Line 15, change "proleferative" to -- proliferative --;
Lines 16-17, change "angiogentic" to -- angiogenic --;
Line 21, change "proleferative" to -- proliferative --; and
Line 21, change "hypollpidemic" to -- hypolipidemic --.

Signed and Sealed this

Twenty-first Day of May, 2002

Attest:

JAMES E. ROGAN
*Attesting Officer*    *Director of the United States Patent and Trademark Office*